United States Patent
Hersey et al.

(10) Patent No.: US 9,463,226 B2
(45) Date of Patent: Oct. 11, 2016

(54) METHOD FOR TREATING STAGE IV MELANOMA

(76) Inventors: Peter Hersey, New Lambton Heights (AU); Brendon John Coventry, Adelaide (AU)

(*) Notice: Subject to any disclaimer, the term of this patent is extended or adjusted under 35 U.S.C. 154(b) by 1282 days.

(21) Appl. No.: 12/294,670

(22) PCT Filed: Mar. 28, 2006

(86) PCT No.: PCT/AU2006/000408
§ 371 (c)(1),
(2), (4) Date: May 10, 2010

(87) PCT Pub. No.: WO2007/109825
PCT Pub. Date: Oct. 4, 2007

(65) Prior Publication Data
US 2010/0221289 A1 Sep. 2, 2010

(51) Int. Cl.
*A61K 39/00* (2006.01)
*A61K 39/285* (2006.01)
*A61K 31/00* (2006.01)
*A61K 35/768* (2015.01)

(52) U.S. Cl.
CPC ............ *A61K 39/0011* (2013.01); *A61K 31/00* (2013.01); *A61K 35/768* (2013.01); *A61K 2039/5152* (2013.01)

(58) Field of Classification Search
None
See application file for complete search history.

(56) References Cited

U.S. PATENT DOCUMENTS 6,165,502 A * 12/2000 Oleske et al. ................ 424/450

FOREIGN PATENT DOCUMENTS

WO  WO01/70938 * 9/2001

OTHER PUBLICATIONS

Mitchell et al (Cancer Research, vol. 48, pp. 5883-5893).*
Sondak et al (Seminars in Cancer Biology, 2003, vol. 13, pp. 409-415).*
Cassel et al (Cancer, 1977, vol. 40, pp. 672-679).*
Murray et al (Cancer, 1977, vol. 40, pp. 680-686).*
The abstract of Kadison et al (Surgical Clinics of North America, 2003, vol. 83, pp. 343-370).*
Lachmann (Springer Seminars in Immunopathology, 1988, vol. 10, pp. 301-304).*
Bleumink et al (Cancer, 1974, vol. 33, pp. 911-915).*
Friend et al (Immunology, 1973, vol. 25, pp. 869-874).*
Hersey (World Journal of Surgery, 1992, vol. 251-260).*
Coventry et al (Journal of Cancer Therapy, 2010, vol. 1, pp. 205-213).*
Miller et al (Journal of Immunology, 1976, vol. 117, pp. 1519-1526).*
Berd et al (Annals of the New York Academy of Science, 1993, vol. 690, pp. 147-152).*
Bystryn, J-C., et al., "Double-Blind Trial of Polyvalent, Shed-Antigen, Melanoma Vaccine," *Clinical Cancer Research*, vol. 7, pp. 1882-1887 (Jul. 2001).
Hersey, P., et al., "Adjuvant Immunotherapy of Patients with High-Risk Melanoma Using Vaccinia Viral Lysates of Melanoma: Results of a Randomized Trial," *Journal of Clinical Oncology*, vol. 20(20), pp. 4181-4190 (Oct. 15, 2002).
Hersey, P., et al., "Phase I/II study of immunotherapy with T-cell peptide epitopes in patents with stage IV melanoma," *Cancer Immunol Immunother*, vol. 54, pp. 208-218 (2005).
Lotem, M., et al., "Autologous cell vaccine as a post operative adjuvant treatment for high-risk melanoma patients (AJCC stages III and IV)," *British Journal of Cancer*, vol. 86, pp. 1534-1539 (2002).
Mitchell, M., et al., "Phase I Trial of Large Multivalent Immunogen Derived from Melanoma Lysates in Patients with Disseminated Melanoma," *Clinical Cancer Research*, vol. 10, pp. 76-83 (Jan. 1, 2004).
Mitchell, M., "Cancer vaccines, a critical review—Part I," *Current Opinion in Investigational Drugs*, vol. 3(1), pp. 140-149 (2002).
Vaishampayan, U., et al., "Active Immunotherapy of Metastatic Melanoma with Allogeneic Melanoma Lysates and Interferon α," *Clinical Cancer Research*, vol. 8, pp. 3696-3701 (Dec. 2002).
Wallack, M., et al., "Surgical Adjuvant Active Specific Immunotherapy for Patients with Stage III Melanoma: The Final Analysis of Data From a Phase III, Randomized, Double-Blind, Multicenter Vaccinia Melanoma Oncolysate Trial," *J. Am Coll Surg*, vol. 187(1), pp. 69-79 (1998).

* cited by examiner

*Primary Examiner* — Karen Canella
(74) *Attorney, Agent, or Firm* — Kilpatrick Townsend & Stockton LLP

(57) ABSTRACT

The present invention relates to a method of treating Stage IV melanoma in a subject. The method includes the step of administering to the subject a therapeutically effective amount of a melanoma cell lysate and/or an immunotherapeutic extract, component or antigen thereof.

16 Claims, No Drawings

US 9,463,226 B2

METHOD FOR TREATING STAGE IV MELANOMA

CROSS-REFERENCES TO RELATED APPLICATIONS

This application is a U.S. National Stage Application of PCT/AU2006/00408, filed Mar. 28, 2006, which is incorporated herein by reference.

FIELD OF THE INVENTION

The present invention relates to a method of treating Stage IV melanoma in a subject, and to a combination product for treating Stage IV melanoma.

The present invention further relates to methods for inhibiting formation and/or growth of tumours in a subject with Stage IV melanoma, improving the rate of survival/life expectancy of a subject with Stage IV melanoma, and inducing an anti-tumour immune response in a subject with Stage IV melanoma.

The present invention also relates to a method of selecting a subject with Stage IV melanoma suitable for treatment.

BACKGROUND OF THE INVENTION

Melanoma is a malignant tumor of melanocytes, cells that are derived from the neural crest. Melanoma can spread by local extension (through lymphatics) and/or by hematogenous routes to distant sites. Any organ may be the site for metastases, but lungs and liver are common sites.

In humans subjects, clinical staging of melanoma is based on whether the tumor has spread to regional lymph nodes or distant sites. Human patients with Stage IV, or metastatic melanoma, have cancer that has spread from its site of origin to distant lymph nodes and/or distant sites. Additional prognostic factors for Stage IV melanoma include site of distant metastases and elevated blood enzyme LDH levels.

The American Joint Committee on Cancer (AJCC) has designated staging by TNM classification to define melanoma. Stage IV melanoma is defined by the following clinical stage grouping: any primary tumor (T), any metastasis to a regional lymph node (N), and a distant metastasis (M).

Overall, AJCC Stage IV melanoma has a dismal survival of 6-9 months from diagnosis and only a 1-2% 5 year survival. However, more advanced Stage IV melanoma with widespread or rapidly appearing metastases has an even shorter survival time of some 3-6 months, with essentially a zero 5 year survival. Surgery for isolated metastases is an option for a subgroup of patients with Stage IV melanoma, and occasionally chemotherapy can be effective in specific instances, but these options are usually not available for widespread metastatic disease and response rates to any form of standard therapy are almost universally non-existent.

Despite many studies relating to the development of therapeutic interventions for melanoma, there has been little progress in this field. Indeed, apart from surgical intervention and the use of chemotherapeutic agents, there is no effective treatment for Stage IV melanoma. The present invention relates to a method of treating Stage IV melanoma by the use of a vaccine produced from melanoma cells.

A reference herein to a patent document or other matter which is given as prior art is not to be taken as an admission that that document or matter was known or that the information it contains was part of the common general knowledge as at the priority date of any of the claims.

SUMMARY OF THE INVENTION

The present invention provides a method of treating Stage IV melanoma in a subject, the method including the step of administering to the subject a therapeutically effective amount of a melanoma cell lysate and/or an immunotherapeutic extract, component or antigen thereof.

The present invention also provides a method of inhibiting formation and/or growth of a secondary tumour in a subject with Stage IV melanoma, the method including the step of administering to the subject a therapeutically effective amount of a melanoma cell lysate and/or an immunotherapeutic extract, component or antigen thereof.

The present invention also provides a method of inhibiting growth of a primary melanoma in a subject with Stage IV melanoma, the method including the step of administering to the subject a therapeutically effective amount of a melanoma cell lysate and/or an immunotherapeutic extract, component or antigen thereof.

The present invention also provides a method of improving the rate of survival of a subject with Stage IV melanoma, the method including the step of administering to the subject a therapeutically effective amount of a melanoma cell lysate and/or an immunotherapeutic extract, component or antigen thereof.

The present invention also provides a method of increasing life expectancy of a subject with Stage IV melanoma, the method including the step of administering to the subject a therapeutically effective amount of a melanoma cell lysate and/or an immunotherapeutic extract, component or antigen thereof.

The present invention also provides a method of inducing an anti-tumour immune response in a subject with Stage IV melanoma, the method including the step of administering to the subject a therapeutically effective amount of a melanoma cell lysate and/or an immunotherapeutic extract, component or antigen thereof.

The present invention also provides use of a melanoma cell lysate, and/or an immunotherapeutic extract, component or antigen thereof, in the preparation of a medicament for treating Stage IV melanoma in a subject.

The present invention also provides a combination product including the following components:
  a melanoma cell lysate and/or an immunotherapeutic extract, component or antigen thereof; and
  either or both of a chemotherapeutic agent and an agent that reduces the level and/or activity of regulatory T cells in the subject;
  wherein the components are provided in a form for separate administration to the subject; or wherein the components are provided in a form for separate administration of the chemotherapeutic agent and co-administration of the lysate and the agent that reduces the level and/or activity of regulatory T cells.

The present invention also provides a method of selecting a subject with Stage IV melanoma suitable for treatment with a melanoma cell lysate, the method including the step of identifying a subject that shows a T cell response upon vaccination of the subject with a melanoma cell lysate and/or an immunotherapeutic extract, component or antigen thereof.

The present invention also provides a method of selecting a subject with Stage IV melanoma suitable for treatment with a melanoma cell lysate, the method including the step of identifying a subject that has a decreased level and/or activity of regulatory T cells upon vaccination of the subject with a melanoma cell lysate and/or an immunotherapeutic extract, component or antigen thereof.

The present invention arises from clinical studies into the use of a Vaccinia Melanoma Cell Lysate (VMCL) vaccine to treat patients with Stage IV metastatic melanoma. The cell lysate is prepared from a melanoma cell line. The studies show that VMCL vaccine appears to be effective in slowing melanoma growth in over 50% of patients and inducing complete regression of tumour in about 25% of patients with advanced "incurable" Stage IV metastatic melanoma. These are patients for which no other effective treatment currently exists. The vaccine also provides a non-toxic avenue for treatment of patients with Stage IV melanoma.

These studies are in contrast to earlier clinical studies that have shown no statistically apparent benefit for VMCL vaccination over an untreated control group in Stage IIb and III patients at 8 years (Hersey et at (2002) *J Clin Oncol* 20:4181-4190).

In addition, patients in the present clinical study were further assessed for the effect of combined vaccine immunotherapy and chemotherapy with Dacarbazine (DTIC). In some subjects, the combined use of VMCL and chemotherapy appeared to be more effective than expected from either therapy alone.

Various terms that will be used throughout the specification have meanings that will be well understood by a skilled addressee. However, for ease of reference, some of these terms will now be defined.

The term "subject" as used throughout the specification is to be understood to mean any human or animal subject. In this regard, the present invention includes within its scope veterinary applications for the treatment of melanoma. For example, the animal subject may be a mammal, a primate, a livestock animal (eg. a horse, a cow, a sheep, a pig, or a goat), a companion animal (eg. a dog, a cat), a laboratory test animal (eg. a mouse, a rat, a guinea pig, a bird), an animal of veterinary significance, or an animal of economic significance.

It will also be appreciated that the term "subject" includes within its scope a subject originally diagnosed as suffering from a Stage IV melanoma and subsequently treated for the melamona. Thus, the present invention extends to the treatment of those original subjects with the melanoma lysate of the present invention. For example, the subject may be a human subject suffering from a Stage IV melanoma, treated for the melanoma (eg by surgery) and then subsequently treated with the lysate of the present invention.

The term "treat" and variants thereof as used throughout the specification is to be understood to mean therapeutic intervention with a melanoma cell lysate (and/or an immunotherapeutic extract, component or antigen thereof) of the present invention. For example, the term includes within its scope the therapeutic intervention with the melanoma lysate to have one or more of the following outcomes: (i) inhibit or prevent the growth of the primary tumour in a subject, including reducing the growth of the primary tumour after resection; (ii) inhibit or prevent the growth and formation of one or more secondary tumours in a subject, including tumours in the lymph nodes; (iii) improve the life expectancy of the subject as compared to the untreated state; and (iv) improve the quality of life the subject as compared to the untreated state.

The term "inhibit" as used throughout the specification is to be understood to mean a reduction in the progress of a process, including any one or more of the start, continuation or termination of a process.

GENERAL DESCRIPTION OF THE INVENTION

As mentioned above, in one form the present invention provides a method of treating Stage IV melanoma in a subject, the method including the step of administering to the subject a therapeutically effective amount of a melanoma cell lysate and/or an immunotherapeutic extract, component or antigen thereof.

The present invention is directed to a method of treating Stage IV melanoma using a immunotherapeutic approach, and in particular, treating the melanoma by administering a vaccine derived from melanoma cells.

The subject in the various forms of the present is a human or animal subject. In one form, the subject is a human subject.

In humans, assessment of the clinical staging of melanoma may generally be made by a suitably qualified practioner in the art.

In this regard, the American Joint Committee on Cancer (AJCC) has designated staging in humans by "TNM" classification to define melanoma. Stage IV melanoma is defined by the following clinical or pathological stage grouping: any primary tumor (T), any metastasis to a regional lymph node (N), and the presence of a distant metastasis (M).

In one form of the present invention, the Stage IV melanoma in the various forms of the present invention is advanced Stage IV melanoma.

The melanoma cell lysate in the various forms of the present invention is a lysate that is able to induce an anti-tumour response in the subject, so as to provide an immunotherapeutic effect in the subject. In this regard, the term "lysate" is to be understood to mean the cellular debris and/or fluid produced by lysis of a cell, or an extract, a component including a semi-purified or purified component, or antigen derived from the lysate. The immunotherapeutic approach of the present invention includes administration of one or more of a lysate, an extract of the lysate, a semi-purified or purified component derived from the lysate, and one or more immunotherapeutic antigens derived from the lysate.

Lysis of a melanoma cell may be achieved by a suitable method, for example, by viral lysis. Methods for producing an immunotherapeutic extract of the lysate, an immunotherapeutic component of the lysate (semi-pruified or purified), or one or more antigens present in the lysate with an immunotherapeutic effect are known in the art.

In one embodiment of the present invention, the melanoma cell lysate includes fragmented melanoma cell membranes.

It is appreciated that the lysate in the various forms of the present invention includes either or both of antigens that are, or were derived from, membrane-associated and non-membrane associated antigens. In this regard, the term "membrane-associated" will be understood to mean an antigen that normally is part of a membrane from a melanoma cell, an antigen that is normally bound to a membrane from a melanoma cell, or an antigen that co-purifies with a cell membrane so as to be associated with a cell membrane in the lysate of the present invention.

In one form of the present invention, the lysate includes membrane-associated antigens.

In a further form, the melanoma cell lysate is an allogenic cell lysate. For example, in the case of treating a human subject with the lysate of the present invention, the melanoma cell lysate may be an allogeneic human melanoma cell lysate.

In the case where the lysate includes fragmented cell membranes, the presence of fragmented cell membranes in the melanoma cell lysate may be determined by a suitable method known in the art. For example, the presence of fragmented cell membranes in the lysate may be confirmed by microscopic analysis of the lysate.

In one embodiment, the melanoma cell lysate is a viral lysate. The virus used to produce the lysate may be a naturally occurring strain (or a derivative thereof), or may be a recombinant virus. In the case of a recombinant virus, the recombinant virus may also encode one or more gene products. For example, the recombinant virus may encode an immunostimulating molecule such as a cytokine, a hematopoietic growth factor or a melanoma immunogen.

Methods for producing cell lysates with viruses are known in the art. Generally, to prepare a viral cell lysate, melanoma cells are infected with a suitable virus resulting in lysis of a proportion of the cells. After a suitable period of time, the lysed cells are collected and processed to produce a lysate suitable for administration to a subject.

For example, the cells may be collected, homogenised and subject to centrifugation to produce a supernatant. The pellet resulting after centrifugation may be also further processed, such as by being subjected to one or more freeze-thaw cycles, and combined with the earlier supernatant. The resulting supernatant (either from the centrifugation or when combined with the freeze-thawed cells) may then be subjected to a further high speed centrifugation to sediment the material. The pellet may then be resuspended in saline and the protein and viral content determined. The lysate is then in a form suitable for administration to a subject. The lysate may be further processed to produce an extract of the lysate, a component of the lysate, or purify one or more antigens present in the lysate, each with immunotherapeutic effect In one form, the cell lysate in the various forms of the present invention is a vaccinia virus cell lysate. Methods for producing cell lysates with vaccinia virus are known in the art.

Accordingly, in one embodiment the present invention provides a method of treating Stage IV melanoma in a human subject, the method including the step of administering to the subject a therapeutically effective amount of a human vaccinia melanoma cell lysate and/or an immunotherapeutic extract, component or antigen thereof.

In the case where a recombinant virus is used to prepare the cell lysate, the virus may also encode an antigen such as a melanoma immunogen (e.g. MAGE-1, MAGE-3, BAGE, GAGE, PRAME and NY-ESO-1); melanocyte differentiation antigens (e.g. tyrosinase, Melan-A/MART-1, gp100, TRP-1 and TRP-2); mutated or aberrantly expressed antigens (e.g. MUM-1, CDK4, beta-catenin, gp100 and N-acetylglucosaminyltransferase); and other antigens like B7-1, TA-90, lysosome-associated membrane protein (LAMP), melanocyte-stimulating hormone receptor (MCIR), and p90 calnexin.

Methods for producing recombinant viruses encoding a desired gene product are known in the art. Methods for cloning nucleic acids into viral vectors are known in the art, for example as described in Sambrook, J, Fritsch, E. F. and Maniatis, T. Molecular Cloning: A Laboratory Manual 2nd. ed. Cold Spring Harbor Laboratory Press, New York. (1989).

As discussed above, the melanoma cell lysate may be an allogeneic melanoma cell lysate.

However, it will be appreciated that the melanoma cell lysate in the various forms of the present invention may also be a lysate produced (or derived from) from melanoma cells or cell lines (primary or secondary) from the subject being treated (i.e. an autologous cell lysate), including melanoma cells derived from the primary tumour or a metastasis resected from the patient.

Methods for producing an autologous cell lysate are known in the art. For example, a suitable method for isolating a malignant cell suspension for use as an autologous antigen source is by excision of malignant tissue and mechanically disaggregated using a scalpel in RPMI 1640 medium in a Petri dish. The cell suspension may be rinsed with RPMI 1640 and transferred to a sterile tissue culture plate, RPMI 1640 containing 5% FCS and antibiotics added and cells cultured in a 37° C., 5% $CO_2$ humidified incubator.

Primary or secondary cell lines may also be produced from these cells by a method known in the art.

Procedures for establishing melanoma cell lines are known in the art.

In the case of treatment of a human subject with the melanoma cell lysate of the present invention, the melanoma cell lysate may be for example an allogenic cell line referred to as MM200, as described in Pope et al. (1979) *Pathology* 11:191-195. This cell line has the HLA type A1,3; B7,35; DR2,4. Chromosomal analysis of this cell line showed a nodal number of 76, and a number of marker chromosomes were also revealed by karyotypic analysis (Muir and Gunz (1979) *Pathology* 11:597-606). Antigens known to be expressed in MM200 cells are Tyrosinase, gp100; MART-1; MAGE-A3; MAGE-A10; BAGE; GAGE; XAGE.

In one embodiment, the lysate of the present invention includes a lysate (and/or an immunotherapeutic extract, component or antigen thereof) from MM200 cells.

Other human melanoma cell lines are described in Satyamoorthy et al (1997) *Melanoma Res.* 7 Suppl 2:S35-42.

Human melanoma cells are also available from the American Tissue Culture Collection. Examples of such cells are listed in Table 1.

TABLE 1

| ATCC Melanoma Cell lines | |
|---|---|
| ATCC Number | ATCC Number |
| CRL-11147 | CRL-1675 |
| CRL-7360 | CRL-1676 |
| CRL-7426 | CRL-2807 |
| CRL-7568 | CRL-2809 |
| CRL-7585 | CRL-2813 |
| CRL-7653 | CRL-2811 |
| CRL-7654 | CRL-2808 |
| CRL-7658 | CRL-7425 |
| CRL-7684 | CRL-2500 |
| CRL-7685 | CRL-2806 |
| CRL-7686 | HTB-66 |
| CRL-7687 | CRL-7636 |
| CRL-7690 | CRL-1424 |
| CRL-7691 | CRL-7898 |
| CRL-7724 | CRL-9607 |
| HTB-137 | CRL-7572 |
| HTB-67 | HTB-64 |
| CRL-1974 | CRL-7637 |
| HTB-73 | CRL-2812 |
| HTB-72 | CRL-1619 |
| CRL-1675 | HTB-66 |
| CRL-1676 | CRL-7636 |

TABLE 1-continued

ATCC Melanoma Cell lines

| ATCC Number | ATCC Number |
|---|---|
| CRL-2807 | CRL-1424 |
| CRL-2809 | CRL-7898 |
| CRL-2813 | CRL-9607 |
| CRL-2811 | CRL-7572 |
| CRL-2808 | HTB-64 |
| CRL-7425 | CRL-7637 |
| CRL-2500 | CRL-2812 |
| CRL-2806 | CRL-1619 |
| CRL-9446 | HTB-69 |
| CRL-1579 | HTB-70 |
| CRL-1585 | HTB-71 |
| CRL-1872 | HTB-65 |
| HTB-140 | HTB-67 |
| HTB-63 | HTB-68 |

In one form, the melanoma cells used to produce the lysate in the various forms of the present invention provide at least one HLA class I antigen.

The present invention also provides the use of a melanoma cell lysate (and/or an immunotherapeutic extract, component or antigen thereof) in the preparation of a medicament for treating Stage IV melanoma in a subject.

In one form, the present invention provides the use of a human melanoma cell lysate (and/or an immunotherapeutic extract, component or antigen thereof) in the preparation of a medicament for treating Stage IV melanoma in a human subject.

In another form, the melanoma cell lysate includes fragmented cell membranes. Accordingly, the present invention also provides use of a melanoma cell lysate (and/or an immunotherapeutic extract, component or antigen thereof) in the preparation of a medicament for treating Stage IV melanoma, wherein the melanoma cell lysate includes fragmented melanoma cell membranes.

In one embodiment, the lysate is a vaccinia melanoma cell lysate. Accordingly, the present invention also provides the use of a vaccinia melanoma cell lysate (and/or an immunotherapeutic extract, component or antigen thereof) in the preparation of a medicament for treating Stage IV melanoma.

The melanoma cell lysate of the present invention may also include one or more carriers or adjuvants. An example of an adjuvant is montanide.

The administration of the cell lysate to the subject in the various forms of the present invention may be performed by a suitable method known in the art, and be conducted over a suitable period of time.

In one form, administration is performed using multiple injections administered over a time course which is selected to maximize an immune response in the subject. Accordingly, the administration of the melanoma cell lysate to the subject may include multiple administrations of the cell lysate to the subject during a treatment period.

In a further form, the administration of the melanoma cell lysate to the human subject includes a treatment period of administration every 2 weeks for one or more cycles, followed by a period of administration once a month for one or more cycles, followed by a period of administration once every 3 months for one or more cycles.

For example, in one embodiment the subject receives biweekly vaccinations (eg injections) for 6 weeks, then every month for 6 months, then every three months until stabilization and/or a complete response is achieved.

However, any suitable immunization regimen of the lysate can be used. It will be appreciated that administration of the lysate is not to be restricted to injection, and indeed the lysate may be administered by any conventional route including parenteral and oral routes. Examples of parenteral routes are subcutaneous, intradermal, transcutaneous, intravenous, intramuscular, intraorbital, intracapsular, intrathecal, intraspinal, intracisternal, intranasal and intraperitoneal. In the case of injection, suitable sites of the injection in a human subject are on anterior thighs, anterior upper arms, or the anterior thorax.

It will also be appreciated that the administration of the melanoma cell lysate in the various forms of the present invention also includes within its scope ex vivo treatment of the subject's cells, or a suitably matched donor's cells, and re-introduction into the subject. For example, antigen presenting cells such as dendritic cells may be isolated from the subject and treated or contacted with the melanoma lysate (and/or an immunotherapeutic extract, component or antigen thereof). Methods for isolating antigen presenting cells, such as dendritic cells, are known in the art.

The antigen presenting cells discussed above include antigen presenting cells isolated from a subject, or an antigen presenting cell formed in vitro from a precursor cell. The antigen presenting cells may be present in a mix of one or more types of cell, or alternatively may be substantially purified from other types of cells.

For example, dendritic cells may be isolated directly from a subject, as a mixture of cells enriched for dendritic cells prepared by leukapheresis of peripheral blood from a subject. Alternatively, the isolated dendritic cells may be prepared by obtaining dendritic cell precursor cells and treating them in vitro to form immature dendritic cells, for example as described in Sallustro et al (1994) *J. Exp. Med.* 179:1109-18.

The introduction of treated antigen presenting cells into a subject may be by a suitable method known in the art, including the introduction intravenously into the subject. For example, treated dendritic cells may be introduced into a human subject as described in Lau et al (2001) *J. Immunol.* 24(1):66-78. Typically, $1 \times 10^6$ to $1 \times 10^8$ dendritic cells will be introduced into a human subject. The time period over which introduction of the treated cells occurs will depend on a number of factors, including the extent of the immune response required, the age and body weight of the subject, and the administration of other active agents to the subject.

The dosage levels of the lysate (and/or an immunotherapeutic extract, component or antigen thereof) administered to the subject in the various forms of the present invention are not particularly limited and depend on the mode of administration, the nature of the subject, and the nature of carrier/adjuvant formulation, so that the administration of the melanoma cell lysate (and/or an immunotherapeutic extract, component or antigen thereof) provides a therapeutic effect.

In the case of a vaccinia melanoma cell lysate, a suitable dose for administration is in the range of 0.1-1.0 ml lysate. A further suitable dose for administration is in the range of 0.1-0.5 ml lysate.

The method of treating the subject in the various forms of the present invention may also include the step of selecting a subject suitable for treatment.

In one form, the subject is selected for treatment on the basis that the subject shows a T cell response to a melanoma cell lysate (and/or an immunotherapeutic extract, component or antigen thereof).

Methods for assessing whether a subject shows a T cell response to a melanoma cell lysate, and/or an immunotherapeutic extract, component or antigen thereof, are known in the art. An antigen of the cell lysate will be understood to mean an antigen normally present in the melanoma cell lysate that is involved in the induction of an immune response to a melanoma in the subject.

Accordingly, the present invention also provides a method of selecting a subject with Stage IV melanoma suitable for treatment with a melanoma cell lysate (and/or an immunotherapeutic extract, component or antigen thereof), the method including the step of identifying a subject that shows a T cell response upon vaccination of the subject with a melanoma cell lysate and/or an immunotherapeutic extract, component or antigen thereof.

The subject may also be selected on the basis that the subject that has a decreased level and/or activity of regulatory T cells upon vaccination of the subject with a melanoma cell lysate and/or an immunotherapeutic extract, component or antigen thereof.

Accordingly, in another form the present invention provides a method of selecting a subject with Stage IV melanoma suitable for treatment with a melanoma cell lysate (and/or an immunotherapeutic extract, component or antigen thereof), the method including the step of identifying a subject that has a decreased level and/or activity of regulatory T cells upon vaccination of the subject with a melanoma cell lysate and/or an immunotherapeutic extract, component or antigen thereof.

Regulatory T cells are CD4+CD25+ T cells (reviewed in Terabe and Berzofsky (2004) "Immunoregulatory T cells in tumor immunity." *Curr Opin Immunol* 16(2): 157-62). Methods for assessing the level and/or activity of regulatory T cells are known in the art.

The treatment of Stage IV melanoma in the subject in the various forms of the present invention may also include one or more other interventions, including for example chemotherapy, biological therapy, radiation and resection of the primary or secondary tumours.

In one form, the treatment of Stage IV melanoma in the subject includes the further step of one or more administrations to the subject of an effective amount of a chemotherapeutic agent.

Examples of suitable chemotherapeutic agents include DTIC (Dacarbazine), Temozolomide (Temodal®), and Fotemustine. Suitable dosages are Dacarbazine (DTIC) 850 mg/m$^2$ 3-weekly intravenously; Fotemustine 100 mg/m$^2$ weekly intravenously for 3 weeks, then 4 weekly thereafter; Temazolamide 200 mg/m$^2$ orally day 1-5 initially, then continued if tolerated well.

In this case, the melanoma cell lysate may be administered to the human subject 2 or more weeks prior to an administration of a chemotherapeutic agent, such as Dacarbazine (DTIC). This is done so that an induction of an immune response in the patient may be achieved prior to the reduction in leukocytes due to treatment with the chemotherapeutic agent at 7-10 days.

Biological agents may also be used in the various forms of the present invention in conjunction with the administration of the melanoma cell lysate. Such agents include for example interferons (eg α-interferon), interleukins (eg IL-2), and monoclonal antibodies.

The present invention also provides a combination product including a melanoma cell lysate (and/or an immunotherapeutic extract, component or antigen thereof), and either or both of a chemotherapeutic agent and an agent that reduces the level and/or activity of regulatory T cells in the subject. In such a case, the components will generally be provided in a form for separate administration to the subject. However, it will also be appreciated that the melanoma cell lysate (and/or an immunotherapeutic extract, component or antigen thereof) and the agent that reduces the level and/or activity of regulator T cells may be in a form for co-administration to the subject.

Accordingly, in another form the present invention provides a combination product including the following components:
  a melanoma cell lysate and/or an immunotherapeutic extract, component or antigen thereof; and
  either or both of a chemotherapeutic agent and an agent that reduces the level and/or activity of regulatory T cells in the subject;
wherein the components are provided in a form for separate administration to the subject; or wherein the components are provided in a form for separate administration of the chemotherapeutic agent and co-administration of the lysate and the agent that reduces the level and/or activity of regulatory T cells In one form, the combination product is used to treat Stage IV melanoma in a human subject.

Methods for packaging the various components of the combination medical product are known in the art.

In one form, the cell lysate in the combination product is a viral melanoma cell lysate.

In a further form, the lysate is a vaccinia melanoma cell lysate.

Accordingly, in another form the present invention provides a combination product including the following components:
  a vaccinia melanoma cell lysate and/or an immunotherapeutic extract, component or antigen thereof; and
  either or both of a chemotherapeutic agent and an agent that reduces the level and/or activity of regulatory T cells in the subject;
  wherein the components are provided in a form for separate administration to the subject; or wherein the components are provided in a form for separate administration of the chemotherapeutic agent and co-administration of the lysate (and/or an immunotherapeutic extract, component or antigen thereof) and the agent that reduces the level and/or activity of regulatory T cells.

In one form, the chemotherapeutic agent in the combination product is one or more of Dacarbazine, Temozolomide (Temodal®), and Fotemustine.

The combination product may also be used to inhibit growth of a primary tumour in a human subject, inhibit formation and/or growth of a secondary tumour in a subject, to improve the rate of survival of a subject with Stage IV melanoma, to improve the life expectancy of a subject with Stage IV melanoma, and/or to induce an anti-tumour immune response in a subject with Stage IV melanoma.

The combination product may also include instructions for selecting a subject with Stage IV melanoma suitable for treatment. Such instructions may, for example, include instructions for selecting a subject with Stage IV melanoma suitable for treatment on the basis that the subject shows a T cell response to a melanoma cell lysate or an antigen thereof, and/or selecting a subject on the basis that the subject has a decreased level and/or activity of regulatory T cells upon vaccination of the subject with a melanoma cell lysate, and/or an immunotherapeutic extract, component or antigen thereof.

Accordingly, the combination product may be supplied in the form of a kit for treating Stage IV melanoma.

In the case of surgical interventions used in conjunction with the administration of the melanoma cell lysate in the various forms of the present invention, the method may include the further step of resecting metastases from the subject. In one embodiment, the metastases are resected prior to administration of the human melanoma cell lysate. Metastatic involvement of organs may include skin, subcutaneous tissues, muscle, lung, liver, brain, bowel, spleen and bone.

The present invention may also include the further step of one or more administrations of an effective amount of an agent to the subject that reduces the level and/or activity of regulatory T cells in the subject.

As discussed previously, regulatory T cells are CD4+ CD25+ T cells (reviewed in Terabe and Berzofsky (2004) "Immunoregulatory T cells in tumor immunity." *Curr Opin Immunol* 16(2): 157-62). Methods for assessing the level and/or activity of regulatory T cells are known in the art.

As discussed above, the present invention may be used to prevent and/or slow the growth of secondary tumours in a subject. Thus, the present invention may also be used to inhibit or prevent metastases in the subject.

The extent of formation and growth of primary and secondary tumours in a subject may be monitored by a method known in the art. Monitoring methods include clinical examination and measurement, U/S scans, CT scans, chest X ray, bone X ray, MRI scans, PET scans, and bone scans.

Accordingly, in another form the present invention provides a method of inhibiting formation and/or growth of a secondary tumour in a subject with Stage IV melanoma, the method including the step of administering to the subject a therapeutically effective amount of a melanoma cell lysate and/or an immunotherapeutic extract, component or antigen thereof.

In one form, the lysate includes fragmented melanoma cell membranes.

In a further form, the melanoma cell lysate is a vaccinia lysate.

The present invention may also be used to inhibit or prevent the growth of the primary tumour in a subject, including reducing the growth of the primary tumour after resection or other treatment.

Accordingly, in another form the present invention also provides a method of inhibiting the growth of a primary melanoma in a subject with Stage IV melanoma, the method including the step of administering to the subject a therapeutically effective amount of a melanoma cell lysate and/or an immunotherapeutic extract, component or antigen thereof.

The present invention may also be used to improve the rate of survival of a subject with a Stage IV melanoma. An improved rate of survival can be measured, for example, as an improved survival rate after a given amount of time (eg 5 or 10 years), or an improved median survival time.

Accordingly, in another form the present invention provides a method of improving the rate of survival of a subject with Stage IV melanoma, the method including the step of administering to the subject a therapeutically effective amount of a melanoma cell lysate and/or an immunotherapeutic extract, component or antigen thereof.

In one form, the lysate includes fragmented melanoma cell membranes.

In a further form, the melanoma cell lysate is a vaccinia cell lysate.

Methods for determining the improvement in survival rate are known in the art.

The present invention may also be used to improve the life expectancy of a subject.

Accordingly, in another form the present invention provides a method of increasing life expectancy of a subject with Stage IV melanoma, the method including the step of administering to the subject a therapeutically effective amount of a melanoma cell lysate and/or an immunotherapeutic extract, component or antigen thereof.

The present invention may also be used to improve the outcome for a subject suffering from Stage IV melanoma, and/or improve the quality of life of the subject. Methods for assessing outcome and quality of life parameters are known in the art.

The present invention may also be used to induce an anti-tumour immune response in a subject. In this case, the present invention may be used for eliciting an anti-cancer immune response in a subject by administering a therapeutically effective amount of the melanoma cell lysate (and/or an immunotherapeutic extract, component or antigen thereof).

Accordingly, the present invention also provides a method of inducing an anti-tumour immune response in a subject with Stage IV melanoma, the method including the step of administering to the subject a therapeutically effective amount of a melanoma cell lysate and/or an immunotherapeutic extract, component or antigen thereof.

In one form, the lysate includes fragmented melanoma cell membranes.

In a further form, the melanoma cell lysate is a vaccinia cell lysate.

Accordingly, in one embodiment the present invention provides a method of inducing an anti-tumour immune response in a subject with Stage IV melanoma, the method including the step of administering to the subject a therapeutically effective amount of a vaccinia melanoma cell lysate and/or an immunotherapeutic extract, component or antigen thereof.

Methods for assessing an anti-tumour response in a subject are known in the art.

Induction of anti-melanoma immunity may be determining by a delayed type hypersensitivity (DTH) response against melanoma antigens prior to and at periods after the melanoma vaccine treatment. In addition, serum and peripheral blood lymphocytes may be obtained prior to injection of the vaccine and at periods after the vaccine injection to test the induction of anti-melanoma immunity by cytotoxicity assay, CTL precursor frequency ($CTL_p$) assay and phenotypic analysis of lymphocytes.

In this regard, the administration of the lysate to the subject may also produce one or more of an increase in the number of intratumoral dendritic cells in the subject, an improvement in dendritic cell activation in the subject, and a modulation of the number and/or activity of regulatory T cells in the subject.

General Methods:

Activation, phenotype and function of T cells may be tested through ELISPOT, cytokine assays, cytotoxicity assays and proliferation assays.

IFN-γ and IL4 ELISPOT, antigen specific $^3$H-thymidine incorporation proliferation assay and flow cytometry may be used to analyse regulatory T cells.

For T cell assays, PBMC will be isolated from peripheral blood using standard Ficoll-Hypaque density centrifugation methods. PBMC may be frozen in aliquots suitable for the experiments and thawed when required. Blood from healthy or other volunteers may be used as controls to establish the 'normal' range of responses and background values for the various tests used.

IFN-γ and IL4 ELISPOT assays may be used to test for the frequency of tumour antigen reactive T cells (CTL and T helper cells). Commercially available antibody pairs (R&D systems for IFN-γ and BD Pharmingen for IL4) may be used in a standard ELISPOT protocol. PBMC may be cultured with various antigens in 96-well PVDF membrane microwell plates (Millipore), which have been coated before with the appropriate amount of antibody. Antigens that may be used include VMCL, MM200 lysate, autologous tumour cell lysate (were applicable), Tet-Tox as a recall antigen and PHA as a positive control. PBMC without adding any antigen may be used as a background control.

Antigen specific proliferation of PBMC may be tested using standard $^3$H-thymidine incorporation assays. PBMC will be cultured in 96 well plates in the presence of antigen for 2 to 3 days. $^3$H thymidine may be added for the last 16 h of the culture.

The Miltenyi Cytokine Secretion Assay may be used to detect IFN-γ and IL4 producing T cells in the peripheral blood. This is a very sensitive assay giving information on the frequency of cytokine producing cells. Additionally, cells can be counterstained with cell surface markers to identify the subpopulation of cells. CD3 may be used as a general T cell marker and CD8 to distinguish between CD8 and CD4 T cells as cell surface markers. PBMC cultured overnight (16 h) in the presence of VMCL, MM200 cell lysate or autologous tumour cell lysate (where applicable) may be used in this assay.

Cytotoxicity of activated T cells may be tested with standard calcein-Acetoxymethyl (AM) (Molecular Probes) cytotoxicity assays (Lichtenfels et al. (1994) *J Immunol Methods* 172(2): 227-239; Neri et al. (2001) *Clin Diagn Lab Immunol* 8(6): 1131-1135). This a nonradioactive, very sensitive cytotoxicity assay with comparable results to the chromium release assay. Calcein-AM freely diffuses into most cells. Once inside the cell, this nonfluorescent substrate is converted by nonspecific intracellular esterases into a fluorescent product that are retained by cells with intact plasma membranes. In contrast, the dye will leak from cells with damaged cell membranes and can be detected in the supernatant.

PBMC may be tested for cytotoxicity towards calcein-AM labelled cells either directly after being isolated from the peripheral blood (fresh) or after being cultured in vitro for one week with antigen. Target cells used in this assay would be autologous tumour cells (where applicable), MM200 cells or other HLA-matched melanoma cell lines. Autologous monocyte derived DC (MoDC) pulsed or unpulsed with tumour cell lysate as target cells may be used if no suitable HLA-matched melanoma cell line can be used. MoDC may be generated using standard protocols with IL4 and GMCSF as described in (Heinzel et al. (2001) *Cancer Immunol Immunother* 49(12): 671-8). Target cells may be labelled with calcein-AM for 30 min at 37° C. $10^4$ target cells may be incubated with effector cells (50:1 to 1:1 ratios) for 4 hours. Supernatants may then be transferred to new wells and measured using a Typhoon 9410 (Amersham Biosciences). (Excitation 488 nm, emission 530 nm). Percent lysis is calculated with the same standard formula used for chromium release assays.

Flow cytometry may be used to investigate the phenotype of activated T cells. Fresh PBMC or after 10 day culture in the presence of antigen can be analysed for the expression of markers including CD3, CD4, CD8, CD25, CD16, CD56, CD69, CD45RO.

To test for the cytokine profile of activated T cells, PBMC can be stimulated in vitro in the presence of antigen (MoDC pulsed with MM200 lysate or VMCL). After 10 days of culture, cells can be tested with intracellular cytokine staining and flow cytometric analysis for the production of cytokines Cells may be harvested and stimulated for 4 hours with PHA/Ionomycin in the presence of Brefeldin A. Cytokines suitable for testing include IL2, IL4, IL10, IL13, TNFa and IFN-g. Cells may also be stained with cell surface markers and analysed using three colour flow cytometry. Cell surface markers include CD3, CD8, CD69, CD25 and CD45RO.

The presence of anti-ganglioside antibodies in the sera from patients may be tested. Antiganglioside antibodies may be detected by immunodot-blot. We will coat strips of PVDF-P membranes (Millipore) may be coated with purified commercial GM3, GM2, GD3, GM1, GD1a, GD1b, and GT1b gangliosides (Sigma). The strips can be incubated with 1/100, 1/200, and 1/500 dilutions of the patients' sera. Bound antibodies can be detected with alkaline phosphatase conjugated antibodies to human IgG and IgM. BCIP/NBT will be used as substrate.

PBMC activated in vitro with VMCL and tumour cell lysate may be tested to determine whether a VMCL or tumour specific response can be induced and to test whether the type of T cell activated by VMCL is comparable in vitro and in vivo. Activated T cells may be phenotyped as described above. PBMC can be stimulated in vitro with autologous MoDC pulsed with VMCL, MM200 cell lysate, irradiated MM200 cells, and autologous tumour cell lysate (where applicable). Tet-Tox can be used as a control. After 10 to 14 days of culture T cells may be restimulated once with antigen pulsed MoDC and cultured for another 10-14 days. IL2 may be added to the culture 2 days after restimulation. General activation can be tested with $^3$H-thymidine proliferation assay. Frequency of VMCL or MM200 reactive T cells may be measured with ELISPOT and Miltenyi cytokine secretion assay.

The relative number of CD4+CD25+ T reg cells in the peripheral blood of patients may be determined. This is done by comparing the number of T-regs in patients before and after vaccination; in addition it is also possible to compare the number of CD4+CD25+ T reg cells between different patient groups, namely responders to the vaccine with non-responders, and Stage IV to stage III patients. The frequency of CD4+CD25 T-reg cells can be determined using 3 colour flow cytometry. Cells may be stained with CD4 and CD25 antibodies plus other important markers to define the population as T reg cells. Suitable markers are CD45RA, CD45RO, CD62L, CD122. The population of interest is the CD4$^+$, CD25high population. Most of these cells also express CD45RO, CD62L and CD122 and will not express CD45RA. The T reg (CD4$^+$CD25$^+$) fraction may be assessed in association with the induction of specific CD8$^+$ cells.

To test the functionality of the CD4$^+$CD25high cell population to inhibit normal T cell responses, the CSFE cell division assay may be used (Lyons and Parish (1994) *Immunol Methods* 171(1): 131-7). T cells from peripheral blood can be separated into CD8$^+$ and CD4+ fractions. The CD4+ cell may be further separated into the CD25neg and the CD25high population. The CD25neg population can be stained with CFSE, and activated non-specifically with anti-CD3 and anti-CD28 antibodies or specifically with VMCL or MM200 tumour cell lysate pulsed autologous MoDC and co-cultured for 4 days with or without the CD25high population. Cell division may be determined in the flow cytometer. CD4+CD25+ cells can also be tested for their cytokine production, using intracellular cytokine staining as described above. Cytokines tested for include IL10 and TGF-β.

Unless otherwise indicated, the practice of many aspects of the present invention employs conventional techniques of molecular biology, recombinant DNA technology and immunology, which are within the skill of the art. Such techniques are described in more detail in the scientific literature, for example, Sambrook, J. et al., Molecular Cloning: A Laboratory Manual, 2.sup.nd Ed., Cold Spring Harbor Press, Cold Spring Harbor, N.Y., 1989, Ausubel, F. M. et al. Current Protocols in Molecular Biology, Wiley-Interscience, New York, current volume; Albers, B. et al., Molecular Biology of the Cell, 2.sup.nd Ed., Garland Publishing, Inc., New York, N.Y. (1989); Lewin, B M, Genes IV, Oxford University Press, Oxford, (1990); Watson, J. D. et al., Recombinant DNA, Second Edition, Scientific American Books, New York, 1992; Darnell, J E et al., Molecular Cell Biology, Scientific American Books, Inc., New York, N.Y. (1986); Old, R. W. et al., Principles of Gene Manipulation. An Introduction to Genetic Engineering, 2.sup.nd Ed., University of California Press, Berkeley Calif. (1981); DNA Cloning Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Methods in Enzymology: Guide to Molecular Cloning Techniques, (Berger and Kimmel, eds., 1987); Hartlow, E. et al., Antibodies: A Laboratory Manual, Cold Spring Harbor Laboratory Press, Cold Spring Harbor, N.Y., 1988), Coligan, J. E. et al., eds., Current Protocols in Immunology, Wiley-Interscience, New York 1991.

DESCRIPTION OF THE EMBODIMENTS

Reference will now be made to experiments that embody the above general principles of the present invention. However, it is to be understood that the following description is not to limit the generality of the above description.

Example 1

Vaccine Preparation

Vaccine preparation was carried out as in Hersey et al (1987) *Cancer Immunol. Immunother* 25:257-265, using methods similar to those described by Wallack et al. (1998) *J. Am. Coll. Surg.* 187:69-77 and Wallack et al (1986) *Cancer* 57:649-655.

A single allogeneic melanoma cell line, referred to as MM200 (Pope et al. (1979) *Pathology* 11:191-195), was infected with vaccinia virus (prepared by Commonwealth Serum Laboratories, Melbourne, Australia) at 2.5 pock-forming units/cell. MM200 was originally isolated from a primary melanoma on a 43-year-old woman in 1972 but no other patient details are available. The HLA type was A1,3; B7,35; DR2,4. Chromosomal analysis showed a nodal number of 76, and a number of marker chromosomes were revealed by karyotypic analysis (Muir and Gunz (1979) *Pathology* 11:597-606).

The vaccinia virus was the strain referred to as strain O, which was derived in 1921 from two strains imported from the Lister Institute in 1912 and a strain from Japan imported in 1913. After 24 hours of incubation, the lysed cells were further homogenized with a sterile Dounce (type B pestle) homogenizer and centrifuged at 400×g for 7 minutes. The supernatant (1) was kept and the pellet frozen and thawed in 1 to 3 mL of distilled sterile water. The latter was then made up to 20 mL, centrifuged at 400×g for 7 minutes and the supernatant (2) added to supernatant (1). The pooled supernatant was centrifuged at 38,000×g for 60 minutes and the sediment resuspended in saline to give an equivalent of $5 \times 10^6$ MM200 cells/0.5 mL saline. The vaccine was tested for pathogenic viral, bacterial, or fungal contamination and kept at −80° C. until use.

Example 2

Administration Regime

The VMCL vaccine protocol (vaccination with 0.1-0.5 ml of the lysate) specified 2 weekly vaccinations for 5 cycles, monthly for 4 cycles and then 3 monthly for as long as a measurable observable clinical response was present. Chemotherapy was used for some patients who developed progressive disease despite vaccine therapy. Where chemotherapy was used with VMCL vaccine, the schedule was modified slightly to administer the vaccine in the 1-2 weeks prior to each DTIC dose (given in standard 3 weekly cycles), with the aim of induction of an immune response prior to leukocyte nadir at about 7-10 days. The use of chemotherapy was determined by the patient's condition and consent. The effect was assessed after 3 doses, with CT scans, before a further 3 doses were given.

Patients were given the vaccine by intradermal injection over the deltoids or on the anteromedial aspect of the thighs, rotating to a different site with each injection. The first injection was given at a site opposite to the site of LN dissection. As discussed above, injections were given every 2 weeks for the first 8 weeks, monthly for 4 months, and then 3 monthly for as long as a measurable observable clinical response was present.

For chemotherapy, the general approach was to administer VMCL vaccine therapy first, then if required, include chemotherapy using Dacarbazine, fotemustine, temozolomide (Temodal®), or a combination sequentially, administered synchronously with the VMCL vaccine therapy. In some patients, the chemotherapeutic agents (detailed above) were given or commenced prior to the administration of the VMCL vaccine and this was allowable within the protocol. Standard doses of Dacarbazine (DTIC) were 850 mg/m$^2$ 3-weekly intravenously, Fotemustine 100 mg/m$^2$ weekly intravenously for 3 weeks, then 4 weekly thereafter, and Temazolamide 200 mg/m$^2$ orally day 1-5 initially, then continued if tolerated well.

Example 3

VMCL Stage IV Melanoma Pilot Clinical Study

Data has been obtained for 20 patients with advanced Stage IV Melanoma treated with the VMCL vaccine. These patients would ordinarily be considered to have "incurable" metastatic disease, beyond the capacity for surgical resection of metastases. A range of metastatic sites were present in these patients including subcutaneous, lung, brain, liver, bone and bowel. Patients with brain metastases were excluded at entry. However, if cerebral metastases developed during the study these were then resected where possible and adjuvant radiotherapy was used post-surgery.

These patients were then re-induced with VMCL vaccine after recovery, repeating the initial protocol. Several patients with prior resected and treated cerebral metastases were included.

As discussed above, the VMCL vaccine protocol specified 2 weekly vaccinations for 5 cycles, monthly for 4 cycles and then 3 monthly for as long as a measurable observable clinical response was present. Chemotherapy was used for some patients who developed progressive disease despite vaccine therapy. Where chemotherapy was used with VMCL vaccine, the schedule was modified slightly to administer the vaccine in the 1-2 weeks prior to each DTIC dose (given in standard 3 weekly cycles), with the aim of induction of an immune response prior to leukocyte nadir at about 7-10 days. The use of chemotherapy was determined by the patient's condition and consent. The effect was assessed after 3 doses, with CT scans, before a further 3 doses were given. Occasionally, another chemotherapeutic agent was used.

The spectrum of the clinically definable responses to VMCL vaccine treatment observed in the pilot study ranged from, no clinically apparent objective response, slowing of disease progression, stabilisation of disease (no apparent growth of metastatic lesions), measurable partial regression of lesions, to induction of complete regression of all objectively measurable tumour.

TABLE 1

Study statistics of VMCL clinical pilot study
Median Age 60 years

| | |
|---|---|
| Age Range | 41-84 |
| Breslow thickness Range (primary) | 0.26-10 mm |
| Median Survival | 10 months |
| Survival Range | 2-50 months |
| Survival Complete Responders (median) | 46 months |
| Died | 15 |
| Alive | 5 |

TABLE 2

Results of VMCL clinical pilot study

| | | |
|---|---|---|
| Patients enrolled | 20 | 100% |
| Initial Complete Regression | 5 | 25% |
| Complete Durable Regression (Alive + CR) | 3 | 15% |
| Slowing of Disease Progression | 17 | 85% |
| Partial Regression of Tumour | 12* | 60% |
| Stabilisation of Disease | 5* | 25% |
| Any Clinically Measurable Response | 19 | 95% |
| No Observable Quantifiable Response | 1 | 5% |

[*some "Slowing of Disease Progression", "Partial Regression" and "Stabilisation of Disease" responses occurred in the same patient within different metastases, ie. overlapping populations, occurring either synchronously or chronologically.]

Finally, it will be appreciated that various modifications and variations of the present invention described herein will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are apparent to those skilled in the art are intended to be within the scope of the present invention.

The invention claimed is:

1. A method of treating Stage IV melanoma in a subject, the method including administering to the subject a composition lacking an adjuvant or carrier, the composition comprising a therapeutically effective amount of a vaccinia melanoma cell lysate and/or immunotherapeutic extract thereof, wherein the composition is administered in the absence of an adjuvant or carrier.

2. The method according to claim 1, wherein the subject is a human subject.

3. The method according to claim 1, wherein the cell lysate includes fragmented melanoma cell membranes.

4. The method according to claim 1, wherein the Stage IV melanoma is advanced Stage IV melanoma.

5. The method according to claim 1, wherein the administration of the vaccinia melanoma cell lysate, and/or an immunotherapeutic extract thereof, to the subject includes a treatment period of administration every 2 weeks for one or more cycles, followed by a period of administration once a month for one or more cycles, followed by a period of administration once every 3 months for one or more cycles.

6. The method according to claim 1, wherein the method further includes one or more administrations to the subject of an effective amount of a chemotherapeutic agent.

7. The method according to claim 6, wherein the chemotherapeutic agent is selected from one or more of the group consisting of Dacarbazine, Fotemustine and Temozolomide.

8. The method according to claim 7, wherein the vaccinia melanoma cell lysate and/or immunotherapeutic extract thereof is administered to the subject 1 to 2 weeks prior to the administration of the chemotherapeutic agent.

9. The method according to claim 6, wherein the chemotherapeutic agent is administered after administration of the vaccinia melanoma cell lysate and/or immunotherapeutic extract thereof.

10. The method according to claim 9, wherein the vaccinia melanoma cell lysate and/or immunotherapeutic extract thereof is administered to the subject 1 to 2 weeks prior to the administration of the chemotherapeutic agent.

11. The method according to claim 1, wherein the method further includes one or more administrations of an effective amount of an agent to the subject that reduces the level and/or activity of regulatory T cells in the subject.

12. The method according to claim 1, wherein the method further includes selecting a subject suitable for treatment.

13. The method according to claim 12, wherein the subject is selected on the basis that the subject shows a T cell response to a vaccinia melanoma cell lysate and/or an immunotherapeutic extract thereof.

14. The method according to claim 12, wherein the subject is selected on the basis that the subject has a decreased level and/or activity of regulatory T cells upon administration to the subject of a vaccinia melanoma cell lysate and/or an immunotherapeutic extract thereof.

15. The method according to claim 1, wherein the composition consists of a vaccinia melanoma cell lysate and/or an immunotherapeutic extract thereof.

16. A combination product lacking an adjuvant or carrier, the product including the following components:
a vaccinia melanoma cell lysate, and/or immunotherapeutic extract thereof, and
either or both of a chemotherapeutic agent and an agent that reduces the level and/or activity of regulatory T cells in a subject;
wherein the components are provided in a form for separate administration to a subject; or wherein the components are provided in a form for separate administration of the chemotherapeutic agent and co-administration of the lysate and the agent that that reduces the level or activity of regulatory T cells.

* * * * *